(12) United States Patent
Sharareh et al.

(10) Patent No.: US 8,034,050 B2
(45) Date of Patent: Oct. 11, 2011

(54) CATHETER WITH MICROFABRICATED TEMPERATURE SENSING

(75) Inventors: Shiva Sharareh, Laguna Niguel, CA (US); Michele Migliuolo, Pittsburgh, PA (US); William D. Suh, Cary, NC (US); Jennifer Rogers, Saint Marys, PA (US); Ariel Garcia, Glendora, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 541 days.

(21) Appl. No.: 11/281,203

(22) Filed: Nov. 15, 2005

(65) Prior Publication Data

US 2006/0173449 A1 Aug. 3, 2006

Related U.S. Application Data

(60) Provisional application No. 60/628,507, filed on Nov. 15, 2004.

(51) Int. Cl.
 *A61B 18/14* (2006.01)
(52) U.S. Cl. ............ 606/41; 606/31; 607/102; 600/549
(58) Field of Classification Search .................. 606/34, 606/41; 604/528; 600/374, 462, 549
 See application file for complete search history.

(56) References Cited

U.S. PATENT DOCUMENTS

| | | | |
|---|---|---|---|
| 5,365,940 A * | 11/1994 | Teves | 600/549 |
| 5,380,320 A * | 1/1995 | Morris | 606/33 |
| 5,557,967 A * | 9/1996 | Renger | 73/204.24 |
| 5,582,609 A * | 12/1996 | Swanson et al. | 606/39 |
| 5,606,974 A * | 3/1997 | Castellano et al. | 600/462 |
| 5,800,432 A | 9/1998 | Swanson | |
| 5,810,802 A | 9/1998 | Panescu et al. | |
| 5,849,028 A | 12/1998 | Chen | |
| 5,893,885 A | 4/1999 | Webster, Jr. | |
| 5,913,856 A * | 6/1999 | Chia et al. | 606/41 |
| 5,935,124 A | 8/1999 | Klumb et al. | |
| 5,964,757 A | 10/1999 | Ponzi | |
| 5,991,650 A * | 11/1999 | Swanson et al. | 600/374 |
| 6,017,338 A | 1/2000 | Brucker et al. | |
| 6,162,184 A | 12/2000 | Swanson et al. | |
| 6,197,021 B1 | 3/2001 | Panescu et al. | |
| 6,256,525 B1 | 7/2001 | Yang et al. | |

(Continued)

FOREIGN PATENT DOCUMENTS

WO WO 01/64283 A1 9/2001

(Continued)

OTHER PUBLICATIONS

International Search Report mailed Mar. 20, 2006 for International Application No. PCT/US2005/041579.

(Continued)

*Primary Examiner* — Michael Peffley
(74) *Attorney, Agent, or Firm* — Christie, Parker & Hale, LLP (57) ABSTRACT

A catheter with temperature sensing has a catheter body and a tip section with an integrated thermosistive temperature sensor on its outer surface. The temperature sensor includes a microfabricated thin film assembly of which one layer is a sensor layer of thermoresistive material. In one embodiment, the tip section has a flexible tubing with a temperature sensor on its outer surface. In another embodiment, the tip section has an extended tip electrode with a temperature sensor on its outer surface.

20 Claims, 11 Drawing Sheets

U.S. PATENT DOCUMENTS

| | | | |
|---|---|---|---|
| 6,280,440 B1 | 8/2001 | Gocho | |
| 6,293,943 B1 | 9/2001 | Panescu et al. | |
| 6,350,262 B1 | 2/2002 | Ashley | |
| 6,374,143 B1* | 4/2002 | Berrang et al. | 607/137 |
| 6,405,078 B1 | 6/2002 | Moaddeb et al. | |
| 6,466,818 B1 | 10/2002 | Moaddeb et al. | |
| 6,477,396 B1 | 11/2002 | Mest et al. | |
| 6,494,882 B1* | 12/2002 | Lebouitz et al. | 606/45 |
| 6,602,242 B1* | 8/2003 | Fung et al. | 604/528 |
| 7,527,625 B2 | 5/2009 | Knight et al. | |
| 7,771,422 B2 | 8/2010 | Auge, II et al. | |
| 2003/0004506 A1 | 1/2003 | Messing | |
| 2003/0120271 A1 | 6/2003 | Burnside et al. | |
| 2004/0082950 A1* | 4/2004 | Edwards et al. | 606/41 |
| 2004/0161949 A1* | 8/2004 | Yadav et al. | 438/800 |
| 2005/0222564 A1 | 10/2005 | Plaza | |
| 2006/0184165 A1 | 8/2006 | Webster, Jr. et al. | |
| 2006/0235314 A1 | 10/2006 | Migliuolo et al. | |
| 2007/0203481 A1* | 8/2007 | Gregg et al. | 606/34 |

FOREIGN PATENT DOCUMENTS

| | | |
|---|---|---|
| WO | WO 03/103522 A1 | 12/2003 |
| WO | WO 2004/069030 A2 | 8/2004 |

OTHER PUBLICATIONS

Mexican Search Report dated Sep. 8, 2009 issued on corresponding Application No. MX/a/2007/005890 together with transmittal dated Oct. 1, 2009 translating Mexican Search Report highlights.

EPO Communication pursuant to Article 94(3)EPC dated Dec. 29, 2010, 5 pgs.

* cited by examiner

CATHETER WITH MICROFABRICATED TEMPERATURE SENSING

CROSS-REFERENCE TO RELATED APPLICATION(S)

This application claims priority of U.S. Provisional Patent Application No. 60/628,507, filed Nov. 15, 2004.

FIELD OF THE INVENTION

The present invention relates to a catheter having a temperature sensor, in particular, a catheter with a microfabricated temperature sensor integrated thereon to provide interfacial temperature measurement at or near a distal tip.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

In certain applications, it is desirable to have the ability to inject and/or withdraw fluid through the catheter. This is accomplished by means of an irrigated tip catheter. One such application is a cardiac ablation procedure for creating lesions which interrupt errant electrical pathways in the heart.

A typical ablation procedure involves the insertion of a catheter having a tip electrode at its distal end into a heart chamber. A reference electrode is provided, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60.degree. C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

In a typical application of RF current to the endocardium, circulating blood provides some cooling of the ablation electrode. However, there is typically a stagnant area between the electrode and tissue which is susceptible to the formation of dehydrated proteins and coagulum. As power and/or ablation time increases, the likelihood of an impedance rise also increases. As a result of this process, there has been a natural upper bound on the amount of energy which can be delivered to cardiac tissue and therefore the size of RF lesions. Historically, RF lesions have been hemispherical in shape with maximum lesion dimensions of approximately 6 mm in diameter and 3 to 5 mm in depth.

In clinical practice, it is desirable to reduce or eliminate impedance rises and, for certain cardiac arrhythmias, to create larger lesions. One method for accomplishing this is to monitor the temperature of the ablation electrode and to control the RF current delivered to the ablation electrode based on this temperature. If the temperature rises above a preselected value, the current is reduced until the temperature drops below this value. This method has reduced the number of impedance rises during cardiac ablations but has not significantly increased lesion dimensions. The results are not significantly different because this method still relies on the cooling effect of the blood which is dependent on location in the heart and orientation of the catheter to endocardial surface.

Another method is to irrigate the ablation electrode, e.g., with physiologic saline at room temperature, to actively cool the ablation electrode instead of relying on the more passive physiological cooling of the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the tip. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. The coolant flow rate must be balanced against the amount of fluid that can be injected into a patient and the increased clinical load required to monitor and possibly refill the injection devices during a procedure. In addition to irrigation flow during ablation, a maintenance flow, typically at a lower flow rate, is required throughout the procedure to prevent backflow of blood flow into the coolant passages. Thus reducing coolant flow by utilizing it as efficiently as possible is a desirable design objective.

In view of the foregoing, accurate and real-time temperature measurement at a catheter tip providing actual interfacial temperature is desirable. Typical temperature sensors for use with catheters can be up to 30 degrees off from the actual tissue temperature. An ablation catheter with improved temperature sensing capabilities should prevent thrombus formation and tissue charring. It would also provide better tissue/blood contact interface temperature reading allowing an operator better power control. Improved temperature measurement would also have applications to other catheter-based technologies, such as esophagus, VT and other applications where tissue monitoring is a key measurement at a catheter tip.

For improved sensing capabilities, Micro-Electro-Mechanical Systems (MEMS) offer the integration of mechanical elements, sensors, actuators, and electronics on a common silicon substrate through microfabrication technology. MEMS components are typically made using microfabrication processes that can form very thin layers, and compatible "micromachining" processes that selectively etch away parts of a silicon wafer or add new structural layers to form mechanical and electromechanical devices.

Sensor technology that can be integrated into semiconductor materials for sensing characteristics including temperature are well known in the art. A temperature gauge can be constructed using a resistor made of a material such as polysilicon, or other thermoresistive material, whose resistance changes with temperature. Using this type of a sensor, temperature can be measured as a function of the change in the resistance of the material. Furthermore, a temperature gauge can also be constructed by forming a thin film thermocouple.

Accordingly, there exists a need for a catheter with improved temperature sensing capabilities, including an ablation catheter with a microfabricated temperature sensor positioned on the outer surface at or near the distal tip for real time, actual interfacial temperature measurement.

SUMMARY OF THE INVENTION

The present invention is directed to a catheter having a catheter body with proximal and distal ends, and a tip section at the distal end of the catheter body that is equipped with a temperature sensor on its outer surface. The temperature sensor includes a microfabricated thin film assembly of which one layer is a sensor layer of thermoresistive material. In one embodiment, the tip section has a flexible tubing on whose outer surface the temperature sensor is positioned. In another embodiment, the tip section has a tip electrode on whose outer surface the temperature sensor is positioned.

In yet another more detailed embodiment of the catheter, the tip section has multiple sensor layers, each of which detects temperature at or near the distal tip of the catheter. Each sensor layer has a source lead wire and a return lead wire for signal communication with a control system to detect the interfacial temperature at or near the location of each sensor by means of a change in resistance in each sensor layer.

BRIEF DESCRIPTION OF THE DRAWINGS

These and other features and advantages of the present invention will be better understood by reference to the following detailed description when considered in conjunction with the accompanying drawings, wherein.

DESCRIPTION OF THE PREFERRED EMBODIMENTS

Figure 1:
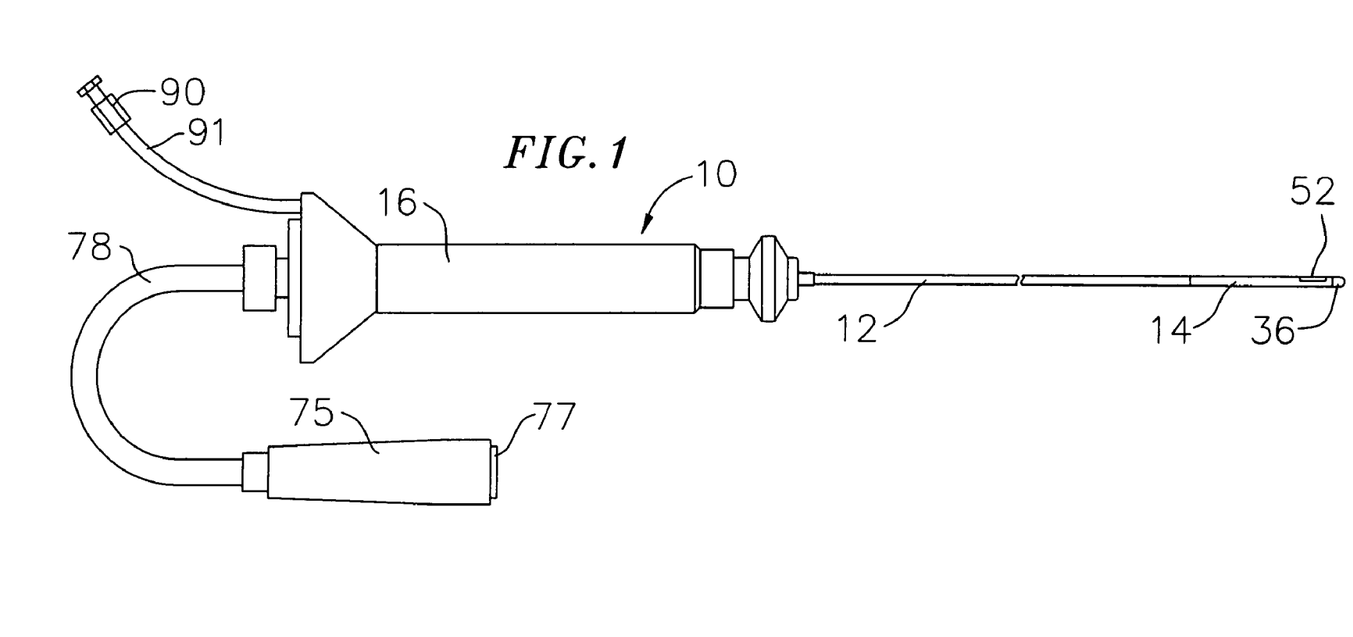
FIG. 1 is an elevated side view of one embodiment of the catheter according to the present invention.

The present invention provides a catheter with improved temperature sensing capabilities. As shown in FIG. 1, a catheter 10 comprises an elongated catheter body 12 having proximal and distal ends, a tip section 14 at the distal end of the catheter body 12 with a temperature sensor 52, and a control handle 16 at the proximal end of the catheter body 12.

Figure 2:
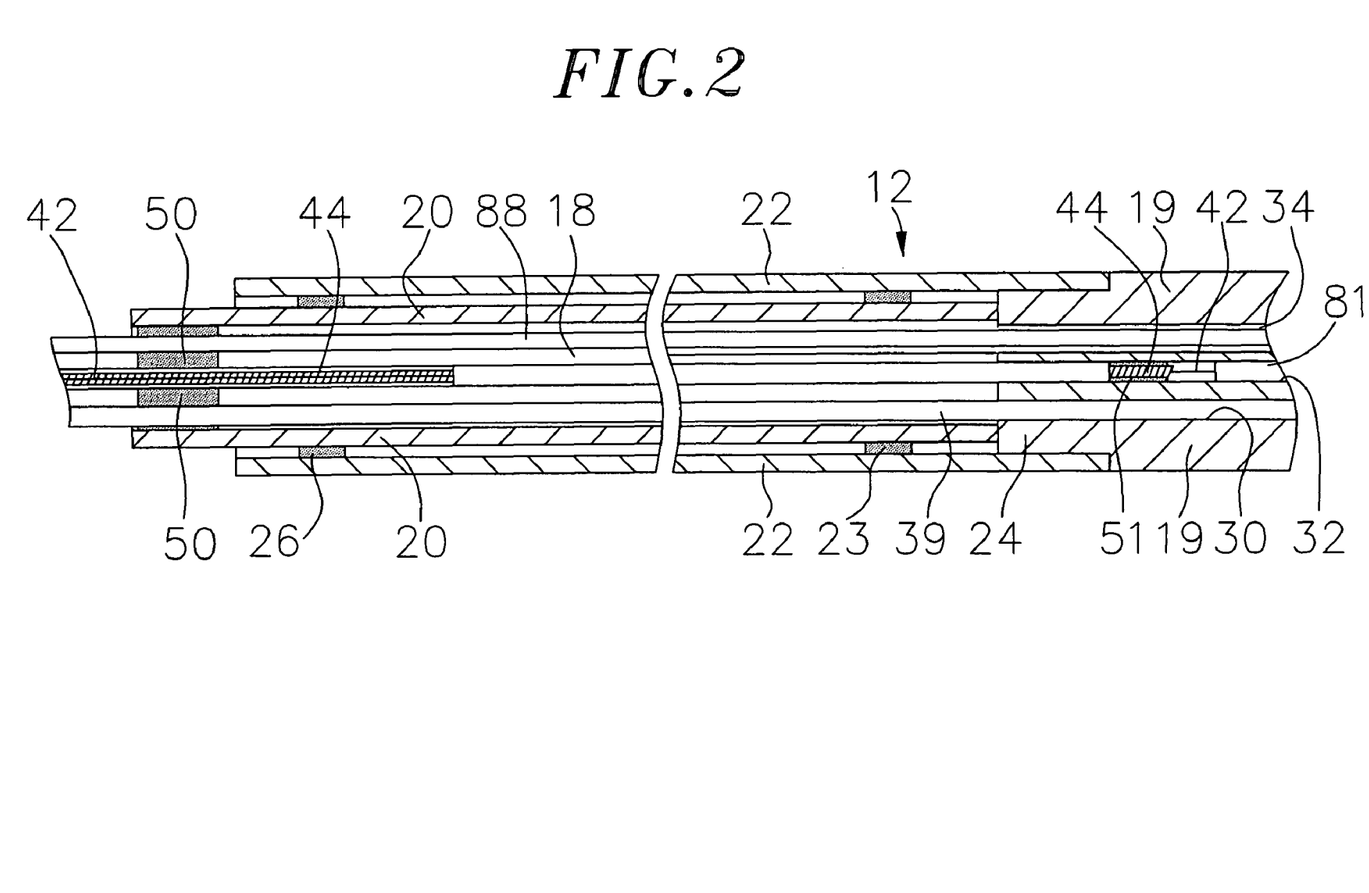
FIG. 2 is a side cross-sectional view of a catheter body according to the catheter of FIG. 1, including the junction between the catheter body and the distal tip section.

With reference to FIGS. 1 and 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

Extending through the single lumen 18 of the catheter body 12 are lead wires, an infusion tube, and a compression coil through which a puller wire 42 extends. A single lumen catheter body may be preferred with certain applications over a multi-lumen body because it has been found that the single lumen body permits better tip control when rotating the catheter. The single lumen permits the lead wires, infusion tube, and the puller wire surrounded by the compression coil to float freely within the catheter body. If such wires and tube were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate an infusion tube, a puller wire, lead wires, and any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness.

An embodiment of the catheter has an outer wall 22 with an outer diameter of from about 0.090 inch to about 0.94 inch and an inner diameter of from about 0.061 inch to about 0.065 inch and a polyimide stiffening tube 20 having an outer diameter of from about 0.060 inch to about 0.064 inch and an inner diameter of from about 0.051 inch to about 0.056 inch.

Figure 3:
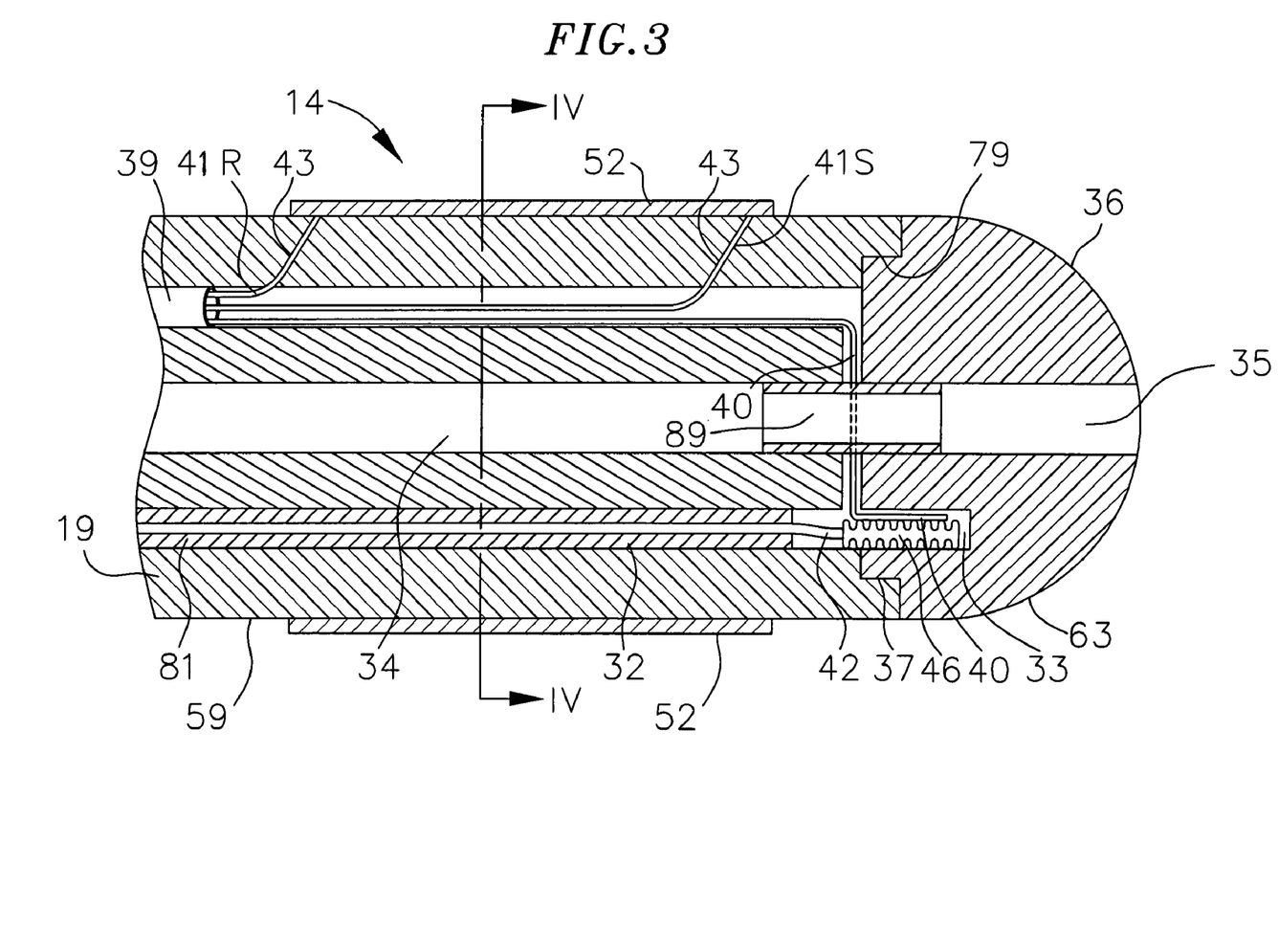
FIG. 3 is a side cross-sectional view of an embodiment of a catheter tip section with a temperature sensor on a flexible tubing.
Figure 4:
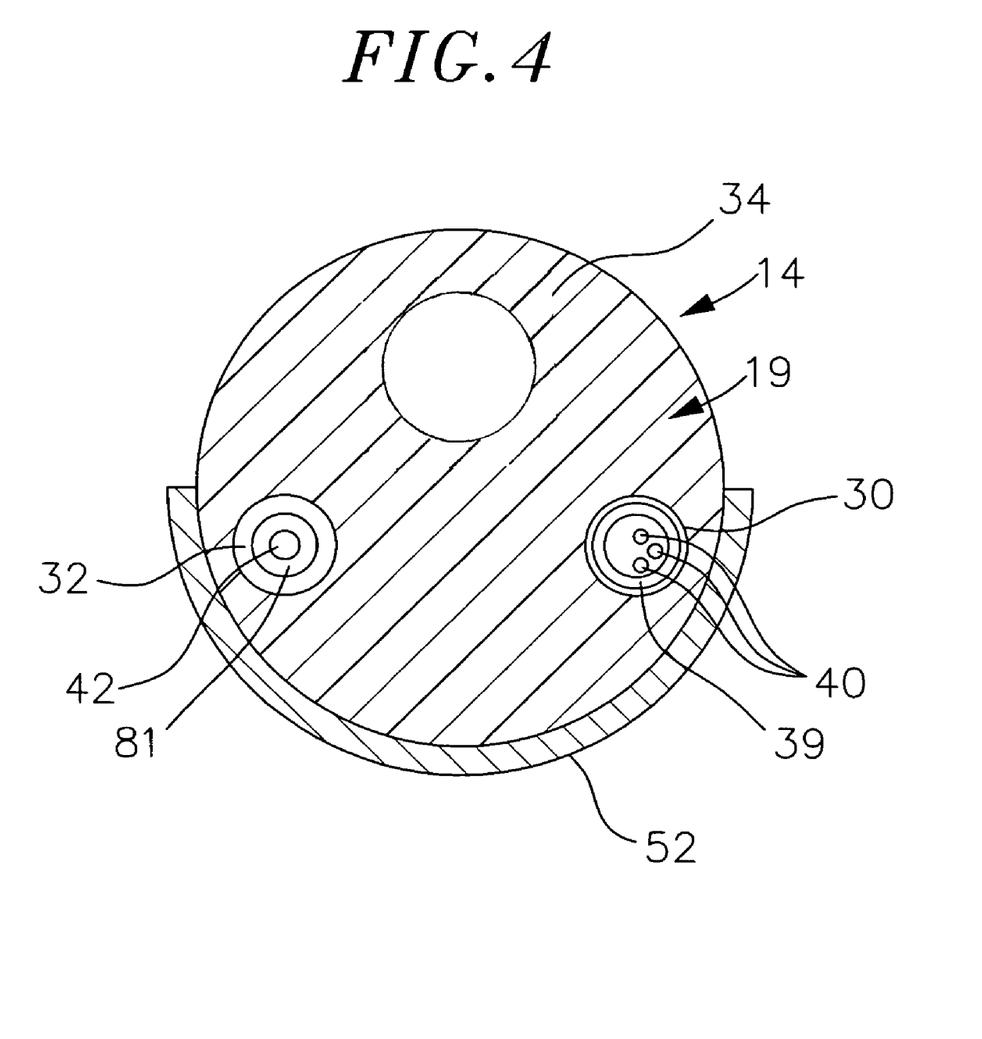
FIG. 4 is a longitudinal cross-sectional view of the tip section illustrated in FIG. 3 taken across line IV-IV.

As shown in FIGS. 3 and 4, the tip section 14 comprises a short section of tubing 19 having three lumens, and a tip electrode 36 distal of the tubing 19. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 french, more preferably 7 french. The size of the lumens is not critical. In an embodiment, the tubing 19 has an outer diameter of about 7 french (0.092 inch) and the first lumen 30 and second lumen 32 are generally about the same size, each having a diameter of from about 0.020 inch to about 0.024 inch, preferably 0.022 inch, with the third lumen 34 having a slightly larger diameter of from about 0.032 inch to about 0.038 inch, preferably 0.036 inch.

A means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and tip section, which allows this junction to bend smoothly without folding or kinking. A catheter having such a spacer is described in U.S. patent application Ser. No. 08/924,616, entitled "Steerable Direct Myocardial Revascularization Catheter", the disclosure of which is incorporated herein by reference.

At the distal end of the tip section 14 is the tip electrode 36. The tip electrode 36 has a diameter about the same as the outer diameter of the tubing 19. As illustrated in FIG. 3, the tip electrode 36 of this embodiment is generally solid, having a fluid passage 35 and a blind hole 33 that corresponds in size and location to the lumen 34 in the tip section 14. The blind hole 33 extends from the proximal end of the tip electrode 36, but does not extend through to the distal end of the tip electrode. It is understood that the configuration of the fluid passage may vary as desired. Other suitable tip designs are disclosed in U.S. Pat. Nos. 6,602,242, 6,466,818, 6,405,078 and U.S. application Ser. No. 10/820,480 filed Apr. 2, 2004, the entire disclosures of which are incorporated herein by reference.

The tip electrode of FIG. 3 has an effective length, i.e., from its distal end to the distal end of the tubing, of about 3.5 mm, and an actual length, i.e., from its distal end to its proximal end, of about 4.0 mm. As shown in FIG. 3, this tip electrode 36 is attached to the tubing 19 by creating a notch 37 in the distal end of the tubing 19 which receives a stem 31 formed in the proximal end of the tip electrode 36, and filling the notch 37 with glue. The wires and tubes that extend into the tip electrode 36 help to keep the tip electrode in place on the tip section 14. The tip electrode 36 can be made of any suitable material, and are preferably machined from platinum-iridium bar (90% platinum/10% iridium).

Figure 9:
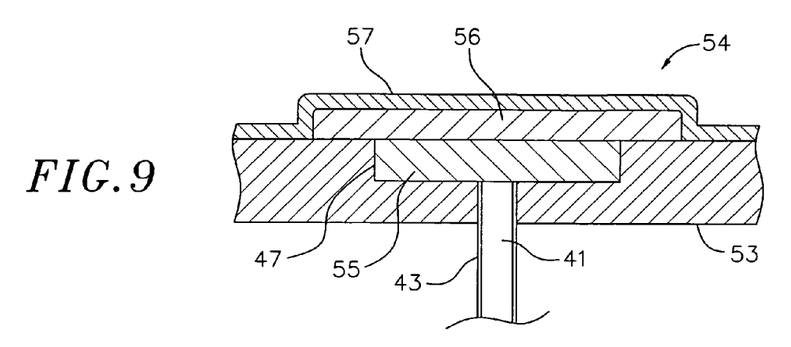
FIG. 9 is a side cross-sectional view of an embodiment of a temperature sensor integrated on a flexible tubing of the catheter.

In accordance with the present invention, the catheter 10 of FIG. 1 has tip section 14 with a temperature sensor 52 on its outer surface. As shown in FIG. 9, the temperature sensor 52 is a microfabricated thin film assembly 54 that includes a thermoresistive sensor layer or film 56 that may be made of any suitable material, for example, polysilicon, nickel, silicon, platinum and/or other thermoresistive material. . The thin film assembly 54 is directly deposited onto a substrate 53, which in the embodiment of FIGS. 3 and 4 is the outer wall 59 of the tubing 19 of the section 14. In the embodiment of FIG. 9, the film assembly 54 includes a contact layer 55 and a protecting coating (or encapsulation layer) 57, with the sensor layer 56 being deposited therebetween. In another embodiment, the film assembly 54 may include a base (or insulation) layer between the contact layer and the substrate.

The sensing layer 56 is a few millimeter in length along the catheter longitudinal axis ranging between about 5.0 mm and 0.1 mm, preferably about 2.0 mm and 1.0 mm, and more preferably about 1.0 mm and 0.1 mm. The sensor layer 56 is a few millimeter in width ranging between about 2.0 mm and 0.1 mm, preferably about 2.0 mm and 1.0 mm, and more preferably about 1.0 mm and 0.1 mm. The sensor layer 56 extends circumferentially around the tip section 14 and may span between about 90 to 270 degrees, preferably about 135 to 225 degrees, more preferably about 180 degrees around the tip section 14. In the illustrated embodiment of FIGS. 3 and 4, the sensor layer 56 spans about 180 degrees around the tip section 14. The sensor layer 56 is about 500 nanometers or less in thickness, preferably ranging between 500 nm and 100 nm and more preferably about 300 and 100 nm. The sensor layer 56 is positioned proximal of a distal end of the tip electrode 36 at a distance of about 5.0 mm, preferably about 3.0 mm and more preferably about 1.0 mm.

Figure 6A:
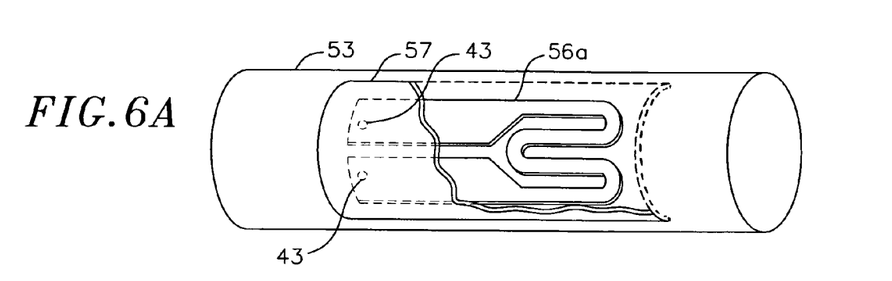
FIG. 6a is an elevated side view of one embodiment of a temperature sensor.
Figure 6B:
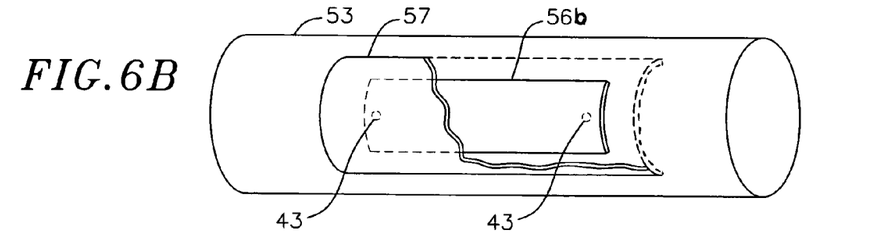
FIG. 6b is an elevated side view of another embodiment of a temperature sensor.
Figure 6C:
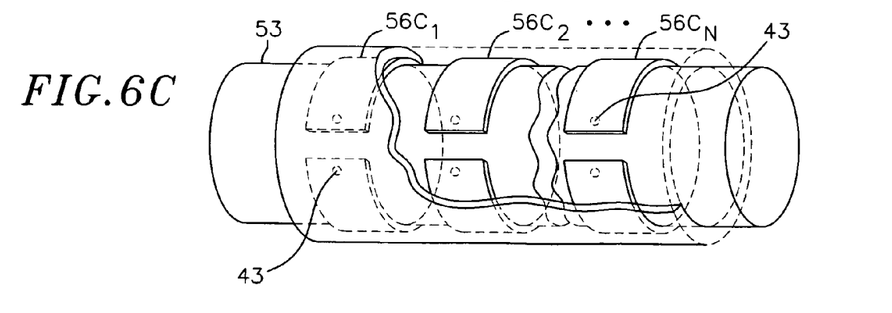
FIG. 6c is an elevated side view of yet another embodiment of multiple temperature sensor.

The plurality and shape of the sensor layer 56 can be varied as desired or appropriate, and in one embodiment, the sensor layer may be lithographically patterned. In the illustrated embodiment of FIG. 6b, there is a sensor layer 56b generally rectangular in shape. In the illustrate embodiment of FIG. 6a, there is a sensor layer 56a having a serpentine pattern, that is, a configuration with at least two changes in direction. In that regard, a serpentine pattern or a pattern with a serpentine component can maximize the resistance of the sensor relative to contact resistances. In the illustrated embodiment of FIG. 6c, there are multiple sensor layers $56c_1$-$56c_N$ each of which can serve as a location for measuring temperature. With multiple sensors or sensors layers on a tip section, the catheter can more easily detect location of hot spots regardless of orientation of the tip electrode with respect to the tissue being ablated.

The temperature sensor 52 is able to measure temperature at or near the distal tip of the catheter. The sensor can be used to monitor tissue temperature and/or catheter tip temperature during treatment of atrial fibrillation symptoms, especially at the tissue-tip interface where most ablation occurs. Thus, the catheter 10 of the present invention provides advantages that include the ability to measure not merely a relative environmental temperature around the tip of the catheter 10 but the interfacial temperature at the catheter tip, and doing so on a real time basis with minimal time delay due to small thermal mass of the sensor. In the area of electrophysiology, there are concerns with tissue overheating that are better managed and addressed by the catheter of the present invention. The catheter 10 provides an operator with an improved monitoring of interfacial temperature to minimize the risks of coagulation and charring of the tissue or other damage to tissue due to overheating.

Figure 7:
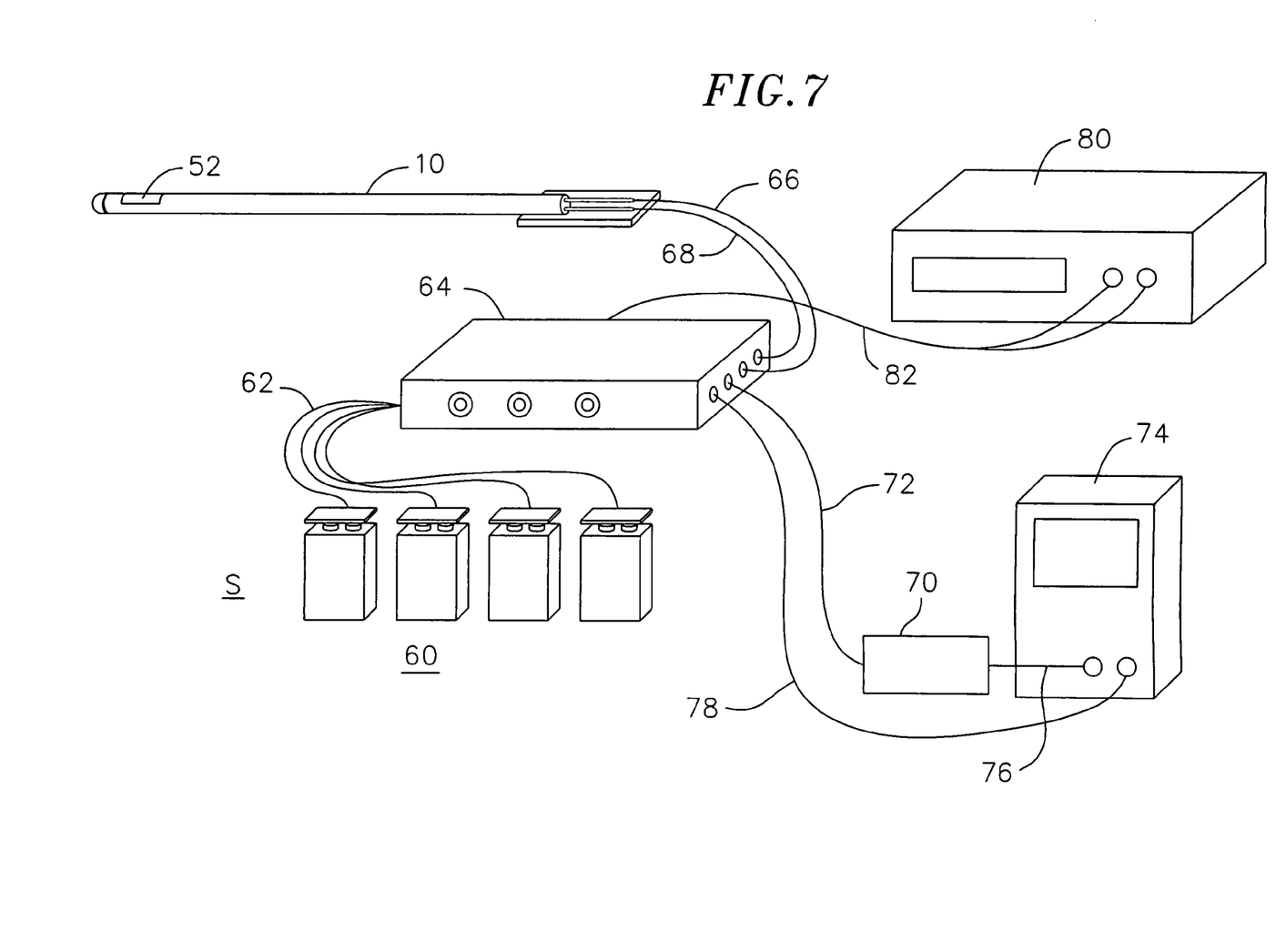
FIG. 7 is a schematic diagram of a system for controlling temperature sensing electronics of the catheter.

Referring back to FIGS. 3 and 4, The tip electrode 36 is connected to a lead wire 40. The sensor 52 is connected to its source lead wire 41s and return lead wire 41r. The lead wires 40 and 41 extend through the first lumen 30 of tip section 14, the central lumen 18 of the catheter body 12, and the control handle 16, and terminate at their proximal end in an input jack (not shown) that may be plugged into an appropriate monitor (not shown) and/or temperature sensing system (FIG. 7). The portion of the lead wires 40 and 41 extending through the central lumen 18 of the catheter body 12, control handle 16 and proximal end of the tip section 14 are enclosed within a protective sheath 39, which can be made of any suitable material, preferably polyimide. The protective sheath 39 is anchored at its distal end to the proximal end of the tip section 14 by gluing it in the second lumen 30 with polyurethane glue or the like.

Connection of the lead wire 40 to the tip electrode 36 is accomplished, for example, by welding the lead wire 40 into the hole 33 in the tip electrode. Connection of the lead wires 41 for the sensor 52 may be accomplished by first making a small hole 43 through the substrate, e.g., tubing 19. Such a hole can be created, for example, by inserting a needle through the tubing 19 and heating the needle sufficiently to form a permanent hole. A lead wire 41 is then drawn through the hole by using a microhook or the like. The end of the lead wire 41 is then stripped of any coating and prepared and treated for connection to the sensor layer 56 as described further below.

Figure 3A:
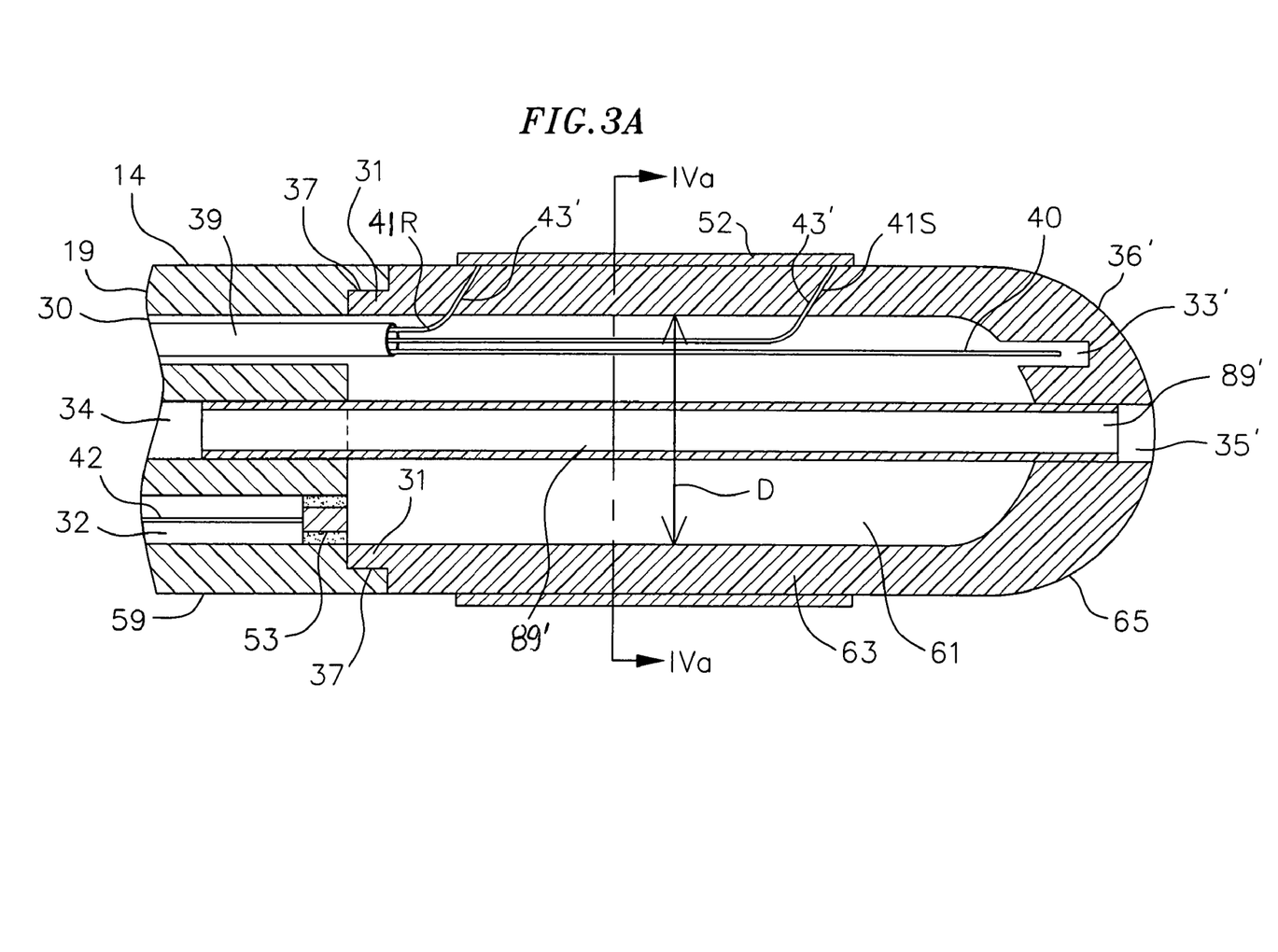
FIG. 3A is a side cross-sectional view of another embodiment of a catheter tip section with a temperature sensor on a tip electrode.
Figure 4A:
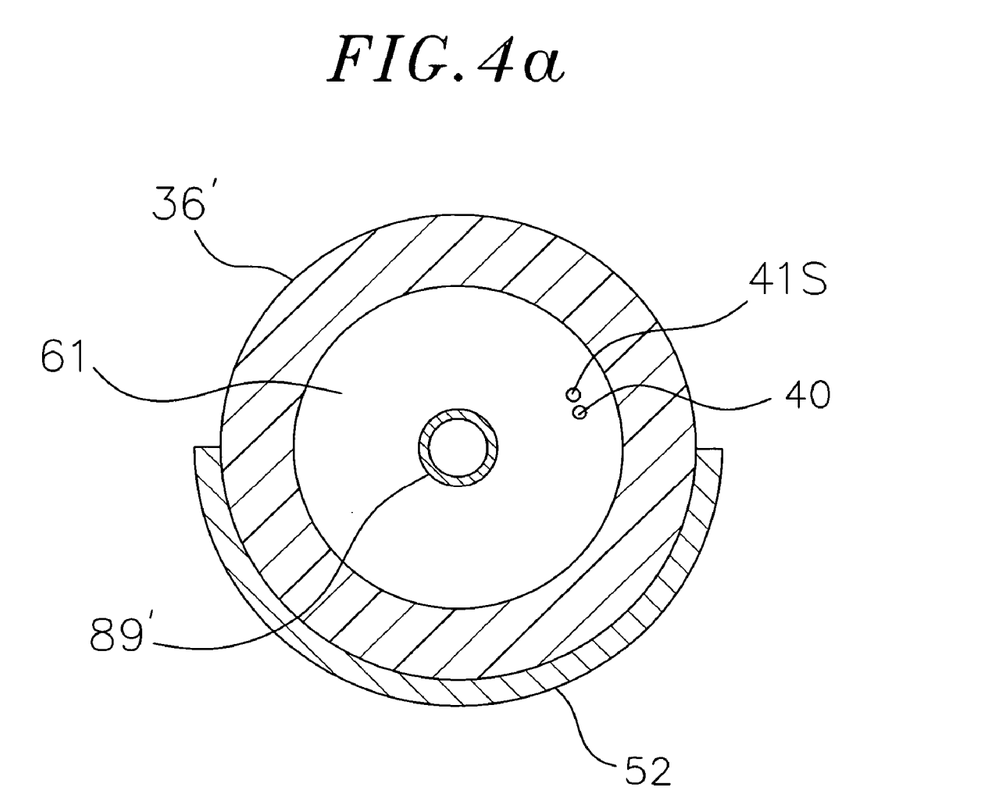
FIG. 4A is a longitudinal cross-sectional view of the tip section illustrated in FIG. 3A taken across line IVA-IVA.

An alternative embodiment of the catheter 10 is illustrated in FIGS. 3A and 4A. A extended tip electrode 36' is connected to the distal end of the tubing 19 of the section 14. The tip electrode 36' has an effective length, i.e., from its distal end to the distal end of the tubing, of about 7.5 mm, and an actual length, i.e., from its distal end to its proximal end, of about 8.0 mm. The tip electrode 36' has a diameter about the same as the outer diameter of the tubing 19 and an open longitudinal core 61 surrounded by a shell 63. The proximal end of the core 61 is in communication with the lumens of the tubing 19. The distal end of the core is proximal of the distal end of the tip electrode 36' and the core is in communication with a fluid passage 35'. An irrigation tube 89' extends from the distal end of the tubing 19 through the core 61 with its distal end in communication with the passage 35. The tip electrode 36' may be formed from a cylindrical rod whose distal end is milled to form an atraumatic conical shape. The rod is then drilled from the proximal end, for example, with a drill bit of a diameter D along the longitudinal axis to form the core. The fluid passage 35' is then formed by drilling from outer surface 65 of the tip electrode 36' toward the core. It is understood that the fluid passage and/or branches thereof may vary as desired. A method of manufacturing a suitable tip electrode is described in U.S. patent application Ser. No. 11/058,434, filed Feb. 14, 2005, entitled Irrigated Tip Catheter and Method of Manufacturing Therefor, the entire disclosure of which is hereby incorporated by reference.

A blind hole 33' is formed in the distal end of the core. The blind hole 33 extends from the distal end of the core but does not extend through to the distal end of the tip electrode. The distal end of a lead wire 40 for the tip electrode 36' is received and, for example, welded in the blind hole 33'.

Figure 9A:
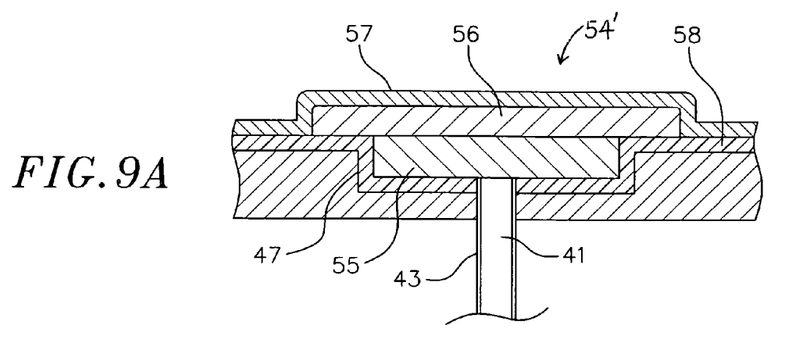
FIG. 9A is a side cross-sectional view of an alternative embodiment of a temperature sensor integrated on a catheter tip electrode.

In the embodiment of FIGS. 3A and 4A, the substrate 53 onto which the microfabricated thin film assembly 54 is directly deposited is the shell 63 of the tip electrode 36'. As such, the film assembly 54 of this embodiment as shown in FIG. 9A includes the contact layer 55, the sensor layer 56, the protective coating 57, and an insulating layer 58 that is deposited on the outer surface 65 of the shell 63 to insulate the tip electrode 36' from the the contact layer.

Connection of the lead wires 41 for the sensor 52 may be accomplished by first making a small hole 43' through the shell 63 of the tip electrode 36'. Such a hole can be created by any suitable process, for example, by drilling or etching. A lead wire 41 is then drawn through the hole by using a microhook or the like. The end of the lead wire 41 is then stripped of any coating and prepared and treated for connection to the sensor layer 56 as described further below.

The thermistor sensor layer 56 of the sensor 52 acts like a thermally sensitive resistor in that it exhibits a change in electrical resistance with a change in its temperature as reflective of the temperature of the tissue and/or fluid with which it is in contact. In one embodiment, the resistance is generally measured by passing a relatively small, measured direct current through the film and measuring the voltage drop. As such, FIG. 7 shows a connection schematic for the catheter 10. An embodiment of a system S to control temperature sensing electronics of the catheter 10 includes a stable constant voltage power supply 60 connected via connectors 62 to an amplified balanced sensing circuit 64 which sends to and receives signals from the sensor 52 via connector 66 and connector 68, respectively. The sensing circuit 64 outputs signals to a low pass filter 70 via connector 72 and to a digital voltmeter 74 via connector 76. The sensing circuit 64 also outputs signals directly to the digital voltmeter 74 via connector 78. An input power supply 80 supplies power to the sensing circuit 64 via connector 82.

Figure 8:
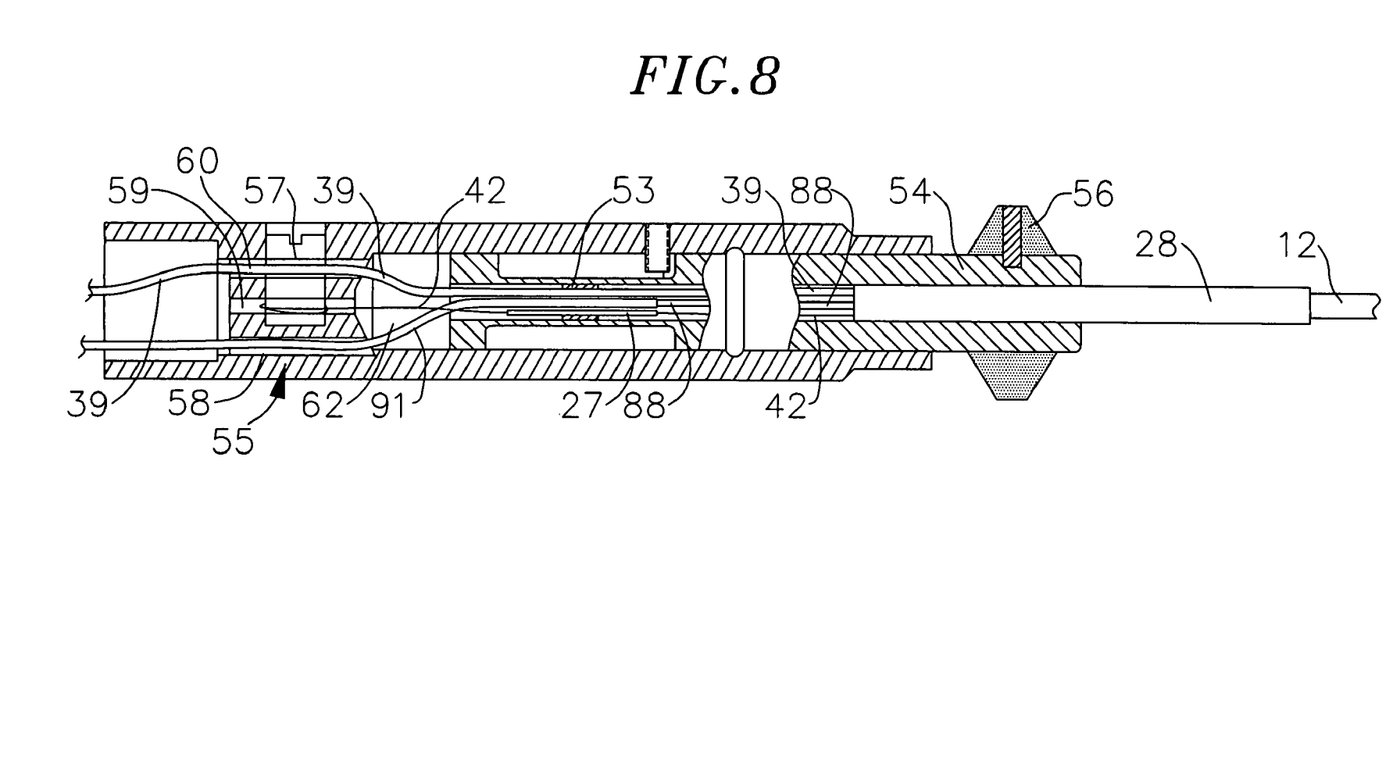
FIG. 8 is a side cross-sectional view of an embodiment of a catheter control handle according to the invention.

In use, a generally steady DC current is passed through the sensor 52 as supplied by the battery bank 60 to the sensing circuit 64 which delivers the current via connector 66. The current output from the sensor 52 is passed back to the sensing circuit 64 via connector 68. The sensing circuit may include conventional logic circuitry for signal conditioning and/or multiplexing particularly where the catheter has more than one sensor 52. The current passes to a low pass filter 70 via connector 72 and to a digital voltmeter 74 via connector 76 before closing the circuit loop with the sensing circuit 64 via connector 78. The voltmeter 74 measures voltage drop that results from a change in resistance of the sensor 52 that results from a change in the temperature of the sensor layer 56. Accordingly, an operator of the catheter can monitor the voltmeter for changes in the interfacial temperature at the catheter distal tip to avoid coagulation and charring of tissue at the ablation treatment site, or any other damage from overheating the tissue The catheter is deflectable by means of a puller wire 42 that extends through the catheter body 12. The puller wire 42 is anchored at its proximal end to the control handle 16 (FIG. 8), and is anchored at its distal end to the tip section 14 (FIGS. 3 and 3A). The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44, shown in FIG. 2, is situated within the catheter body 12 in surrounding relation to the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. The Teflon® coating on the puller wire 42 allows it to slide freely within the compression coil 44. If desired, particularly if the lead wires 40 are not enclosed by a protective sheath 39, the outer surface of the compression coil 44 can be covered by a flexible, non-conductive sheath, e.g., made of polyimide tubing, to prevent contact between the compression coil 44 and any other wires within the catheter body 12.

The compression coil 44 is anchored at its proximal end to the proximal end of the stiffening tube 20 in the catheter body 12 by glue joint 50 and at its distal end to the tip section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

The puller wire 42 extends into the second lumen 32 of the tip section 14. In the embodiment of FIG. 3, the puller wire 42 is anchored at its distal end to the tip electrode 36 within the second blind hole 33. A preferred method for anchoring the puller wire 42 within the tip electrode 36 is by crimping metal tubing 46 to the distal end of the puller wire 42 and soldering the metal tubing 46 inside the blind hole 33. Anchoring the puller wire 42 within the tip electrode 36 provides additional support, reducing the likelihood that the tip electrode 36 will fall off the tip section 14. Alternatively, in the embodiment of FIG. 3A, the puller wire 42 can be anchored in the distal end of the lumen 32 by glue joint 53. In any case, within the second lumen 32 of the tip section 14, the puller wire 42 extends through a plastic, preferably Teflon®, sheath 81, which prevents the puller wire 42 from cutting into the wall of the tip section 14 when the tip section is deflected. Longitudinal movement of the puller wire 42 relative to the catheter body 12 which results in deflection of the tip section, is accomplished by suitable manipulation of the control handle 16. To that end, the control handle and the mechanisms therein can be varied as desired.

An infusion tube is provided within the catheter body 12 for infusing fluids, e.g., saline, to cool the tip electrode 36. The infusion tube may also be used to infuse drugs or to collect tissue or fluid samples. The infusion tube may be made of any suitable material, and is preferably made of polyimide tubing. A preferred infusion tube has an outer diameter of from about 0.32 inch to about 0.036 inch and an inner diameter of from about 0.28 inch to about 0.032 inch.

Figure 5:
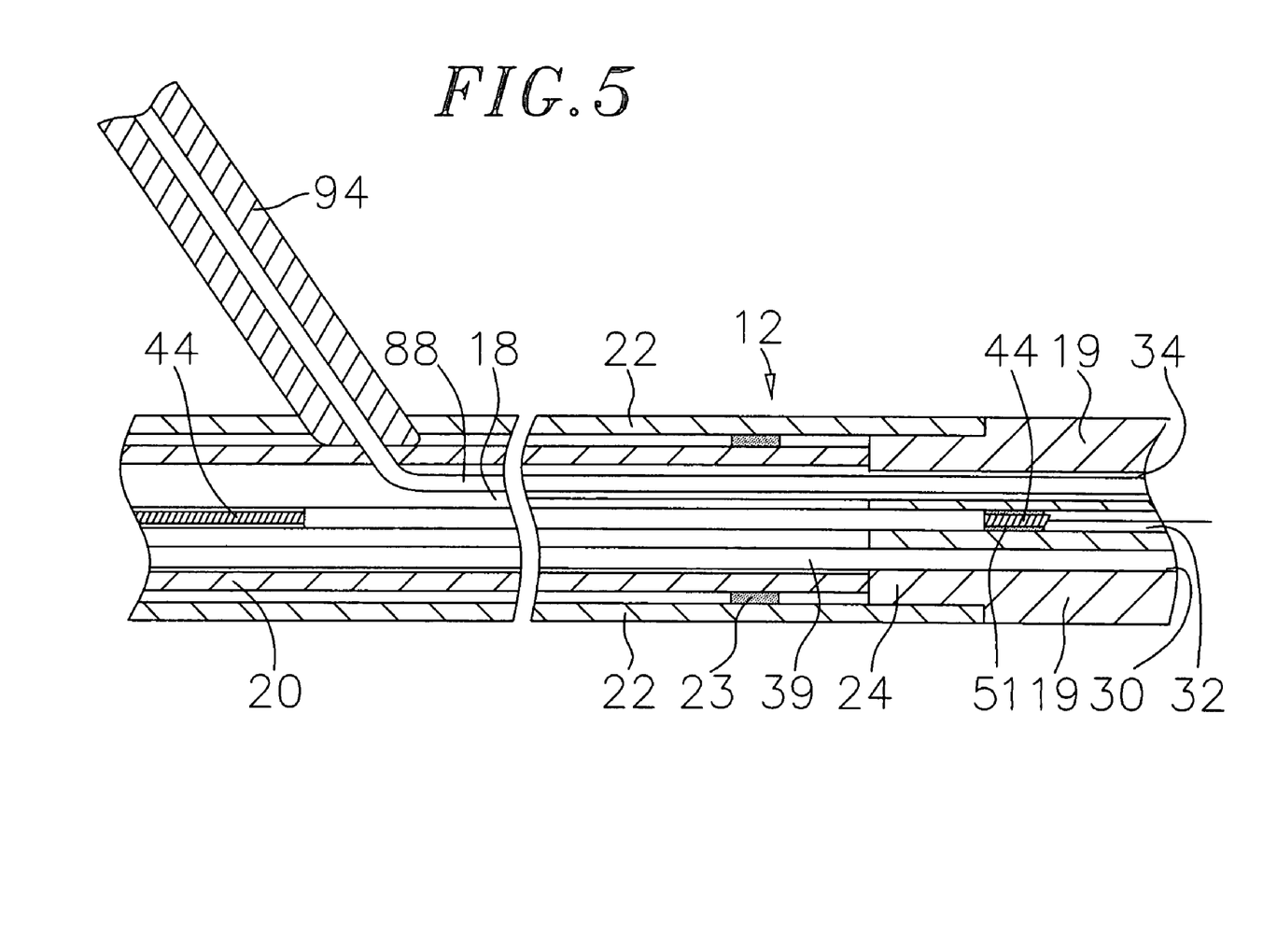
FIG. 5 is a side cross-sectional view of an alternative embodiment of a catheter body according to the invention having a side arm for an infusion tube.

With reference to FIGS. 1, 2 and 5, a first infusion tube segment 88 extends through the central lumen 18 of the catheter body 12 and terminates in the proximal end of the third lumen 34 of the tip section 14. The distal end of the first infusion tube segment 88 is anchored in the third lumen 34 by polyurethane glue or the like. The proximal end of the first infusion tube segment 88 extends through the control handle 16 and terminates in a luer hub 90 or the like at a location proximal to the control handle with reference to FIGS. 3, 3A, 4 and 4A. A second infusion tube segment 89, 89' is provided at the distal end of the third lumen 34 and extends into the fluid passage 35, 35' of the tip electrode 36, 36'. The second infusion tube segment 89, 89' is anchored within the third lumen 34 and the fluid passage 35, 35' by polyurethane glue or the like. The second infusion tube segment 89, 89', like the puller wire 42, provides additional support for the tip electrode. In practice, fluid may be injected into the first infusion tube segment 88 through the luer hub 90, and flows through the first infusion tube segment 88, through the third lumen 34, through the second infusion tube segment, into 89, 89' into the fluid passage 35, 35' in the tip electrode 36, 36', and out the fluid passage 35 in the tip electrode. Again, the fluid passage may have other configurations as desired. In the illustrated embodiments, the fluid passage 35, 35' forms a longitudinal hole that extends out the distal end of the tip electrode, or the tip electrode 36 may be porous enough to allow fluids to pass to the outer surface of the tip electrode, the interconnecting pores forming the fluid passage.

In an alternative arrangement, as shown in FIG. 5, a single lumen side arm 94 is fluidly connected to the central lumen 18 near the proximal end of the catheter body 12. The first infusion tube segment 88 extends through the catheter body 12 and out the side arm 94, where it terminates in a luer hub 90 or the like. The side arm 94 is preferably made of the same material as the outer wall 22, but preferably has a greater thickness, e.g., 0.055 inch. Where the side arm 94 meets the catheter body 12, a molded joint can be provided to provide additional strength and support The molded joint can be made of any suitable biocompatable material, and is preferably made of polyurethane.

FIGS. 6A-6C, 9 and 9A illustrate methods for the microfabrication of the sensor 52 directly on to the substrate 53, which, as mentioned, can be either the tubing 19 of the tip section or the shell 63 of the tip electrode. A plurality of cavities such as pockets 47, holes 43 and slots may be formed in a selected surface of the substrate onto which the sensor 52 is deposited. These can be accomplished by techniques known in the art such as mechanical drilling, boring, laser ablation, EDM, and photochemical etching. Depositions of sensor layer material such as nickel, silicon, polysilicon, platinum and/or other thermoresistive material are realized by various physical and/or chemical deposition techniques known in the art. These include, for example, spin casting, casting, stamping, molding, sputtering, thermal evaporation, PECVD, LPCVD, electroplating, electroless plating, and solgel. The same deposition techniques may be used for creating the insulation coating 58 between metal substrates (e.g., the tip electrode 36') and the sensor layer 56, if appropriate. For example, a thin insulation coating such as parylene; polyimide or a combination of parylene and polyimide may be deposited. The protective coating 57 may also be applied over the sensor layer 56 to protect it from elements, such as blood.

Below is a table showing a method of fabricating the sensor in a small batch process:

| Action | Sub-Action |
| --- | --- |
| Base Layer | Preparation |
|  | Evaporation |
|  | Post-Inspection |
| Contact Layer |  |
| Sensor Layer | Preparation |
|  | Sputtering |
|  | Post-Inspection |
| Encapsulation Layer | Preparation |
|  | Evaporation |
|  | Post-Inspection |

Below is a table showing a method of fabricating the sensor in a large batch process:

| Action | Sub-Action |
| --- | --- |
| Substrate Surface Cleaning | Chemical clean/etc. |
| Base/Insulation Layer | Preparation |
| | Evaporation |
| | Post-Inspection |
| Laser Processing | Preparation |
| | Laser Processing |
| | Post-Inspection |
| Contact Layer | Preparation |
| | Deposition |
| | Post-Inspection |
| Sensor Layer | Preparation |
| | Sputtering |
| | Post-Inspection |
| Encapsulation Layer | Preparation |
| | Evaporation |
| | Post-Inspection |

Suitable detailed manufacturing processes of the sensor 52, the thin film assembly 54 and the sensor layer 56 are described in US patent application "Medical and Surgical Devices with Integrated Sensors", No. PCT/US04/02547, filed in Jan. 30, 2004, which claims priority of U.S. Provisional Patent Application No. 60/443,877 (Jan. 31, 2003), the entire disclosures of both of which are incorporated herein by reference.

The preceding description has been presented with reference to presently preferred embodiments of the invention. Workers skilled in the art and technology to which this invention pertains will appreciate that the Figures are not necessarily to scale and alterations and changes in the described structure may be practiced without meaningfully departing from the principal spirit and scope of this invention. Accordingly, the foregoing description should not be read as pertaining only to the precise structures described and illustrated in the accompanying drawings, but rather should be read consistent with and as support for the following claims which are to have their fullest and fairest scope.

What is claimed is:

1. A catheter comprising:
    a catheter body having proximal and distal ends;
    a tip section at the distal end of the catheter body, the tip section comprising a tip electrode at its distal end and a temperature sensor on an outer surface of the tip electrode, wherein the temperature sensor comprises a contact layer and a thin film sensor layer having a film thickness of about 500 nm or less, wherein the contact layer of the temperature sensor is embedded in a surface of the tip electrode and the thin film sensor layer is on the contact layer and the surface of the tip electrode, the temperature sensor further comprising an insulating layer between the tip electrode and the contact layer.

2. A catheter of claim 1, wherein the sensor layer comprises a thin film thermoresistive material.

3. A catheter of claim 1, wherein the sensor layer has a resistance that changes with changes in temperature.

4. A catheter of claim 1, wherein the sensor further comprises a nonconducting layer.

5. A catheter of claim 4, wherein the nonconducting layer comprises a protective layer.

6. A catheter of claim 4 wherein the nonconducting layer comprises a material selected from the group consisting of parylene, polyimide, and combinations thereof.

7. A catheter of claim 1, wherein the sensor layer comprises a material selected from the group consisting of nickel, platinum, silicon and polysilicon.

8. A catheter of claim 1, wherein the sensor layer is generally rectangular.

9. A catheter of claim 1, wherein the sensor layer has a configuration including a serpentine pattern.

10. A catheter of claim 1, wherein the sensor layer is lithographically patterned onto the outer surface of the tip section.

11. A catheter of claim 1, wherein the catheter is adapted for ablation.

12. A catheter of claim 1, further comprising a control handle at the proximal end of the catheter body.

13. A catheter of claim 1, wherein the tip electrode has at least one fluid passage in fluid communication with a lumen in the tip section, and the catheter comprises an infusion tube having proximal and distal ends, said infusion tube extending through a central lumen in the catheter body and through a lumen in the tip section, and being anchored at its distal end in a proximal end of the fluid passage in the tip electrode, whereby fluid can flow through the infusion tube, into the fluid passage in the tip electrode and through the tip electrode to the outer surface of the tip electrode.

14. A catheter of claim 12, further comprising means for deflecting the tip section by manipulation of the control handle.

15. A catheter according to claim 1, wherein the tip section has three lumens extending therethrough.

16. A catheter according to claim 1, further comprising deflecting means.

17. A catheter of claim 16, wherein the deflecting means comprises a puller wire having a proximal end and a distal end, the puller wire extending from a control handle, through the catheter body and into a lumen in the tip section, wherein the distal end of the puller wire is fixedly secured within the tip section and the proximal end of the puller wire is fixedly secured in the control handle, whereby manipulation of the control handle moves the puller wire relative to the catheter body, resulting in deflection of the tip section.

18. A catheter of claim 1, wherein the catheter is adapted for use with a temperature monitoring system comprising:
    a DC power source supplying a generally steady DC current to pass through the temperature sensor;
    a sensing circuit connected to the temperature sensor to pass said current;
    a voltmeter to measure a change in voltage resulting from a change in resistance of the temperature sensor.

19. A catheter comprising:
    an elongated flexible tubular catheter body having proximal and distal ends;
    a tip section at the distal end of the catheter body, the tip section comprising a tip electrode at its distal end, wherein the tip electrode has on its outer surface an integrated microfabricated temperature sensor having a contact layer and a sensor layer with a thickness of about 500 nm or less, the integrated microfabricated temperature sensor extending circumferentially about 90 to 270 degrees around the tip electrode and wherein the contact layer is embedded in a surface of the tip electrode and the sensor layer is on the contact layer and the surface of the tip electrode, the integrated microfabricated temperature sensor further comprising an insulating layer between the tip electrode and the contact layer.

20. A catheter comprising:
    an elongated flexible tubular catheter body having proximal and distal ends;
    a tip section at the distal end of the catheter body, the tip section comprising a tubing section and an ablation tip electrode at a distal end of the tubing section, wherein the tubing section has on its outer surface an integrated microfabricated temperature sensor having a contact layer and a sensor layer with a thickness of about 500 nm or less, wherein the contact layer is embedded in a surface of the tubing section and the sensor layer is on the contact layer and the surface of the tubing section.

* * * * *